(12) United States Patent
Osaki et al.

(10) Patent No.: US 10,617,368 B2
(45) Date of Patent: Apr. 14, 2020

(54) X-RAY COMPUTED TOMOGRAPHY APPARATUS AND BED DEVICE

(71) Applicant: Canon Medical Systems Corporation, Otawara-shi (JP)

(72) Inventors: Hiroki Osaki, Nasushiobara (JP); Keisuke Oishi, Nasushiobara (JP); Nobuto Tsuchiya, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 30 days.

(21) Appl. No.: 16/025,303

(22) Filed: Jul. 2, 2018

(65) Prior Publication Data

US 2019/0000404 A1   Jan. 3, 2019

(30) Foreign Application Priority Data

Jul. 3, 2017   (JP) ................................ 2017-130476
Jun. 29, 2018  (JP) ................................ 2018-124267

(51) Int. Cl.
*A61B 6/04* (2006.01)
*A61B 6/03* (2006.01)
*A61B 6/00* (2006.01)

(52) U.S. Cl.
CPC ............ *A61B 6/0457* (2013.01); *A61B 6/032* (2013.01); *A61B 6/0407* (2013.01); *A61B 6/488* (2013.01); *A61B 6/54* (2013.01); *A61B 6/4435* (2013.01)

(58) Field of Classification Search
CPC ..... A61B 6/032; A61B 6/0457; A61B 6/4291; A61B 6/4452; A61B 6/4435; A61B 6/488; A61B 6/54; A61B 6/0407
See application file for complete search history.

(56) References Cited

U.S. PATENT DOCUMENTS

| | | | | |
|---|---|---|---|---|
| 4,392,096 A | * | 7/1983 | Grajewski | A61B 6/0442 378/179 |
| 4,475,072 A | * | 10/1984 | Schwehr | A61B 6/0457 378/209 |
| 6,615,428 B1 | * | 9/2003 | Pattee | A61B 6/04 378/209 |
| 2006/0104422 A1 | * | 5/2006 | Iisaku | A61B 6/04 378/209 |
| 2007/0080293 A1 | * | 4/2007 | Huber | A61B 6/032 250/363.02 |

FOREIGN PATENT DOCUMENTS

JP  2006-068123  3/2006
JP  2006-141577  6/2006

* cited by examiner

*Primary Examiner* — Chih-Cheng Kao
(74) *Attorney, Agent, or Firm* — Oblon, McClelland, Maier & Neustadt, L.L.P.

(57) ABSTRACT

One embodiment, control circuitry executes at least one of a start operation and a stop operation. For a start operation, the control circuitry accelerates a top support portion along a forward direction before moving a top when starting to move an object in a scan after positioning the top support portion at a moving start position decided based on a scan condition and accelerates the top to a set speed along the forward direction after a first predetermined time since start of acceleration control on the top support portion. For a stop operation, the control circuitry accelerates the top support portion along the forward direction when decelerating the top and stops the top after a second predetermined time since start of acceleration control on the top support portion.

14 Claims, 13 Drawing Sheets

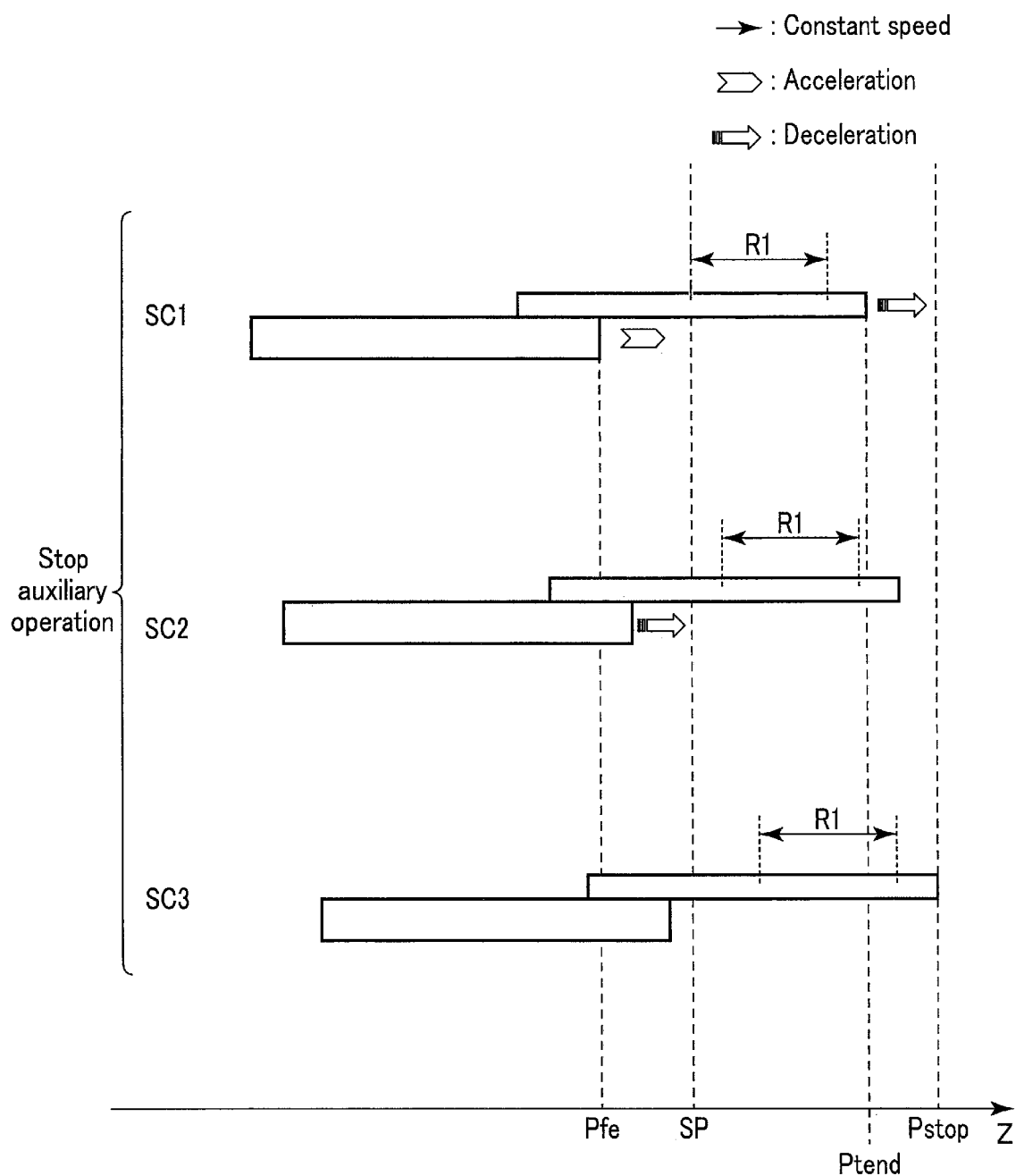
F I G. 13

X-RAY COMPUTED TOMOGRAPHY APPARATUS AND BED DEVICE

CROSS-REFERENCE TO RELATED APPLICATIONS

This application is based upon and claims the benefit of priority from the Japanese Patent Application No. 2017-130476, filed Jul. 3, 2017, and the Japanese Patent Application No. 2018-124267, filed Jun. 29, 2018, the entire contents of all of which are incorporated herein by reference.

FIELD

Embodiments described herein relate generally to an x-ray computed tomography apparatus and a bed device

BACKGROUND

An X-ray computed tomography apparatus includes a bed that slides a top. With the recent increase in imaging speed, an increase in the sliding speed of the top is required. The maximum sliding distance of the top is structurally limited. In order to slide the top at high speed within this limitation, the top must be rapidly accelerated.

BRIEF DESCRIPTION OF THE DRAWING

FIG. 13 is a view schematically showing the operations of the top and the upper frame in a stop auxiliary operation in the high speed mode according to this embodiment;

DETAILED DESCRIPTION

In general, according to one embodiment, an X-ray computed tomography apparatus includes a gantry, a top support portion, a first driving controller, a second driving controller, and control circuitry. The gantry includes an X-ray tube and an X-ray detector. The top support portion supports a top, on which an object is placed, so as to allow the top to move in its longitudinal direction. The first driving controller moves the top in the longitudinal direction. The second driving controller moves the top support portion in the longitudinal direction. The control circuitry executes at least one of a start operation and a stop operation. The control circuitry operates as follows for the start operation. After positioning the top support portion at the moving start position decided based on scan conditions, the control circuitry controls the second driving device to accelerate the top support portion in the forward direction before moving the top at the time of starting to move the object in the scan. After the lapse of a first predetermined time since the start of acceleration control on the frame by the second driving controller, the control circuitry controls the first driving controller to accelerate the top up to a set speed along the forward direction. The control circuitry operates as follows for the stop operation. At the time of decelerating the top, the control circuitry controls the second driving device to accelerate the top support portion in the forward direction. After the lapse of a second time since the start of acceleration control on the top support portion by the second driving controller, the control circuitry controls the first driving controller to stop the top.

The X-ray computed tomography apparatus and the bed device according to this embodiment will be described below with reference to the accompanying drawings.

Figure 1:
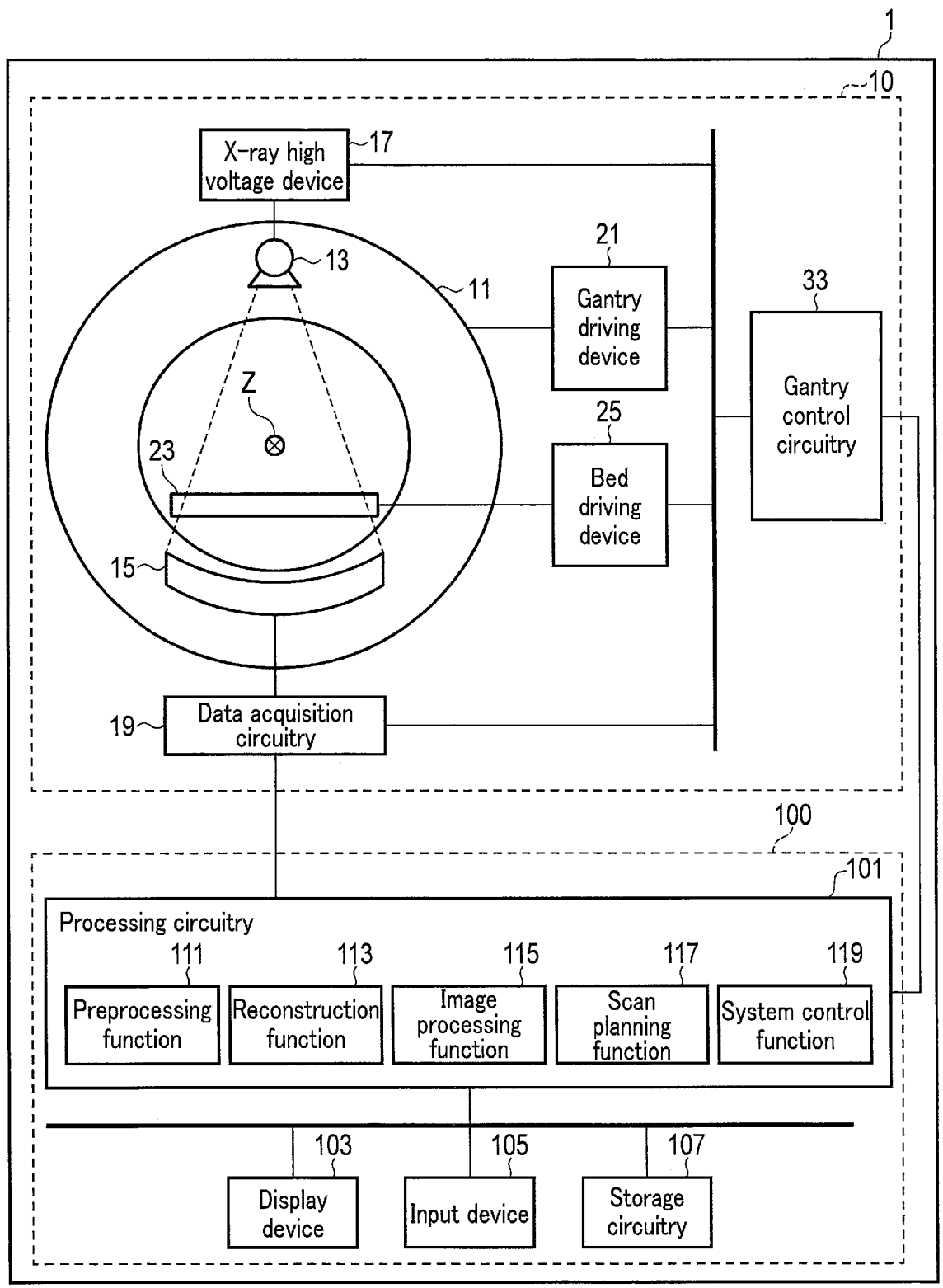
FIG. 1 is a block diagram showing the arrangement of an X-ray computed tomography apparatus according to an embodiment.

FIG. 1 is a block diagram showing the arrangement of an X-ray computed tomography apparatus 1 according to this embodiment. As shown in FIG. 1, the X-ray computed tomography apparatus 1 includes a gantry 10 and a console 100. For example, the gantry 10 is installed in a CT examination room. The console 100 is installed in a control room adjacent to the CT examination room. The gantry 10 is communicably connected to the console 100. The gantry 10 is equipped with an imaging mechanism for X-ray CT imaging. The console 100 is a computer that controls the gantry 10.

As shown in FIG. 1, the gantry 10 includes a rotating frame 11 having an almost cylindrical shape. The rotating frame 11 is also called a rotating portion. As shown in FIG. 1, an X-ray tube 13 and an X-ray detector 15 are mounted on the rotating frame 11 so as to face each other through an opening 41. The rotating frame 11 is a metal frame formed from a metal such as aluminum so as to have an annular shape. The gantry 10 has a main frame formed from a metal such as aluminum. The main frame is also called a fixed portion. The rotating frame 11 is rotatably supported by the main frame.

The X-ray tube 13 generates X-rays. The X-ray tube 13 includes a vacuum tube holding a cathode that generates thermal electrons and an anode that generates X-rays upon receiving thermal electrons flying from the cathode. The X-ray tube 13 is connected to an X-ray high voltage device 17 via a high voltage cable. The X-ray high voltage device 17 applies a tube voltage between the cathode and the anode. Applying the tube voltage makes thermal electrons flying from the cathode to the anode. When thermal electrons fly from the cathode to the anode, a tube current flows.

The X-ray high voltage device 17 can be applied to any type of device such as a transformer type X-ray high voltage device, constant voltage type X-ray high voltage device, capacitor type X-ray high voltage device, or inverter type X-ray high voltage device. The X-ray high voltage device 17 is mounted on, for example, the rotating frame 11. The X-ray high voltage device 17 adjusts X-ray parameters such as a tube voltage and a tube current under the control of gantry control circuitry 33.

As shown in FIG. 1, the rotating frame 11 rotates about a rotation axis Z at a constant angular speed upon receiving power from a gantry driving device 21. In addition, the rotating frame 11 tilts about a tilt axis horizontally perpendicular to the rotation axis Z upon receiving power from the gantry driving device 21. The gantry driving device 21 is housed in, for example, the gantry 10. The gantry driving device 21 generates power for rotating or tilting the rotating frame 11 upon receiving a drive signal from the gantry control circuitry 33. As the gantry driving device 21, an arbitrary motor such as a direct drive motor or servo motor or an actuator is used.

An FOV is set in the opening of the rotating frame 11. The top supported on a bed 23 is inserted into the opening of the rotating frame 11. An object P is placed on the top. The bed 23 movably supports the top. A bed driving device 25 is housed in the bed 23. The bed driving device 25 generates power for moving the top back and forth, up and down, and right and left upon receiving drive signals from the gantry control circuitry 33. The bed 23 positions the top such that an imaging region of the object is included in the FOV.

The X-ray detector 15 detects X-rays generated from the X-ray tube 13. More specifically, the X-ray detector 15 includes a plurality of detection elements arrayed on a two-dimensional curved surface centered on the focus of the X-ray tube. Each detection element includes a scintillator and an optical sensor. The scintillator is formed from a material that converts X-rays into photons. The scintillator converts incident X-rays into light corresponding to a photon quantity corresponding to the incident X-ray dose. The optical sensor is a circuitry element that amplifies light generated from the scintillator and converts the light into an electrical signal. As the optical sensor, for example, a photomultiplier tube, photodiode, or the like is used. Note that the X-ray incident side surfaces of the plurality of scintillators arrayed in the form of a two-dimensional curved surface are provided with a grid including an X-ray shielding material formed in a grid pattern to absorb scattered X-rays. Each detection element may be of an indirect conversion type that detects X-rays after they are converted into photons or a direct conversion type that directly converts X-rays into an electrical signal.

Data acquisition circuitry 19 is connected to the X-ray detector 15. The data acquisition circuitry 19 reads out an electrical signal corresponding to the dose of X-rays, detected by the X-ray detector 15, from the X-ray detector 15, amplifies the read electrical signal with a variable amplification factor, and acquires raw data having a digital value corresponding to the dose of X-rays over a view period by integrating electrical signals over the view period. The data acquisition circuitry 19 is implemented by an ASIC (Application Specific Integrated Circuit) on which a circuitry element that can generate raw data is mounted.

As shown in FIG. 1, the gantry control circuitry 33 synchronously controls the X-ray high voltage device 17, the data acquisition circuitry 19, the gantry driving device 21, and the bed driving device 25 to execute X-ray CT imaging in accordance with scan conditions from processing circuitry 101 of the console 100. The gantry control circuitry 33 according to this embodiment performs a helical scan. The gantry control circuitry 33 includes, as hardware resources, a processing device (processor) such as a CPU (Central Processing Unit) or MPU (Micro Processing Unit) and a storage device (memory) such as a ROM (Read Only Memory) or RAM (Random Access Memory). In addition, the gantry control circuitry 33 may be implemented by an ASIC, FPGA (Field Programmable Gate Array), another CPLD (Complex Programmable Logic Device), or SPLD (Simple Programmable Logic Device).

As shown in FIG. 1, the console 100 includes the processing circuitry 101, a display device 103, an input device 105, and storage circuitry 107. The processing circuitry 101 performs data communication between the display device 103, the input device 105, and the storage circuitry 107 via a bus.

The processing circuitry 101 as hardware resources, a processor such as a CPU, MPU, or GPU (Graphics Processing Unit) and a memory such as a ROM or RAM. The processing circuitry 101 implements a preprocessing function 111, a reconstruction function 113, an image processing function 115, a scan planning function 117, and a system control function 119 by executing various types of programs. Note that the preprocessing function 111, the reconstruction function 113, the image processing function 115, the scan planning function 117, and the system control function 119 may be implemented by the processing circuitry 101 on one substrate or may be separately implemented by processing circuits 101 on a plurality of substrates.

With the preprocessing function 111, the processing circuitry 101 performs preprocessing such as logarithmic conversion of raw data transmitted from the gantry 10. The preprocessed raw data is called projection data.

With the reconstruction function 113, the processing circuitry 101 generates a CT image representing the spatial distribution of CT values concerning the object P based on the preprocessed raw data. As an image reconstruction algorithm, an existing image reconstruction algorithm, for example, an FBP (Filtered Back Projection) method or iterative approximation reconstruction method may be used.

With the image processing function 115, the processing circuitry 101 performs various types of image processing for the CT image reconstructed by the reconstruction function 113. For example, the processing circuitry 101 generates a display image by performing three-dimensional image processing such as volume rendering, surface volume rendering, image value projection processing, MPR (Multi-Planar Reconstruction) processing, or CPR (Curved MPR) processing for the CT image.

With the scan planning function 117, the processing circuitry 101 makes a scanplan automatically or in accordance with an instruction issued by the user via the input device 105.

With the system control function 119, the processing circuitry 101 comprehensively controls the X-ray computed tomography apparatus 1 according to this embodiment. More specifically, the processing circuitry 101 reads out a control program stored in the storage circuitry 107, expands it onto the memory, and controls each unit of the X-ray computed tomography apparatus 1 in accordance with the expanded control program.

The display device 103 displays various types of data such as a scan plan screen and a CT image. As the display device 103, for example, a CRT display, liquid crystal display, organic EL display, LED display, plasma display, or another arbitrary display known in this technical field can appropriately be used.

The input device 105 inputs various types of commands from the user. More specifically, the input device 105 includes an input device and input interface circuitry. The input device accepts various types of commands from the user. As the input device, a keyboard, mouse, trackball, joystick, various types of switches, or the like can be used. The input interface circuitry supplies an output signal from the input device to the processing circuitry 101 via a bus.

The storage circuitry 107 is a storage device such as an HDD, SSD, or integrated circuit storage device that stores various types of information. In addition, the storage circuitry 107 may be a driving device or the like that reads/writes various types of information from/to a portable storage medium such as a CD-ROM drive, DVD drive, or flash memory.

Figure 2:
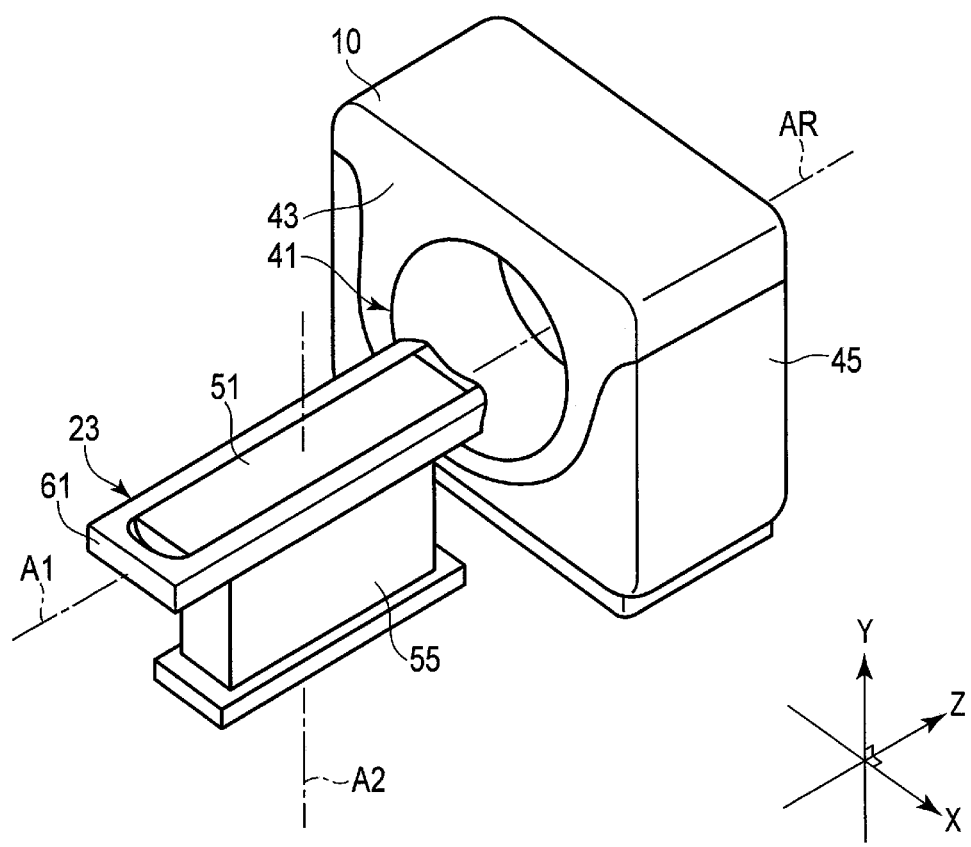
FIG. 2 is a perspective view showing the outer appearance of a gantry according to this embodiment.

FIG. 2 is a perspective view showing the outer appearance of the gantry 10 according to this embodiment. As shown in FIG. 2, the gantry 10 has a gantry main body 43 in which the opening 41 having an almost cylindrical shape is formed. The bed 23 is installed in front of the gantry 10. The bed 23 is a two-stage slide type bed equipped with a top 51, an upper frame 61, and a support base 55. As shown in FIG. 2, the bed 23 is arranged such that a long axis A1 of the top 51 is parallel to a central axis AR of the opening 41.

The top 51 is a plate-like structure having flexibility. The upper frame 61 supports the top 51 so as to allow it to slide along the long axis A1 of the top 51. The support base 55 supports the upper frame 61 so as to allow it to slide along an axis parallel to the long axis A1 of the upper frame 61 and move up and down along a vertical axis A2 vertically perpendicular to the long axis A1. An axis parallel to the long axis A1 is defined as the Z-axis, and an axis parallel to the vertical axis A2 is defined as the Y-axis. An axis perpendicular to the Z-axis and the Y-axis is defined as the X-axis. The XYZ coordinate system forms an orthogonal coordinate system. In addition, a direction parallel to the long axis A1 of the top 51 is called the long-axis direction or the Z direction, and a direction parallel to the vertical axis A2 is called the vertical direction or Y direction. Furthermore, a direction in which the bed 23 approaches the gantry 10 is defined as the +Z direction, a direction in which the bed 23 separates from the gantry 10 is defined as the −Z direction, a direction in which the bed 23 moves up is defined as the +Y direction, and a direction in which the bed 23 moves down is defined as the −Y direction.

Figure 3:
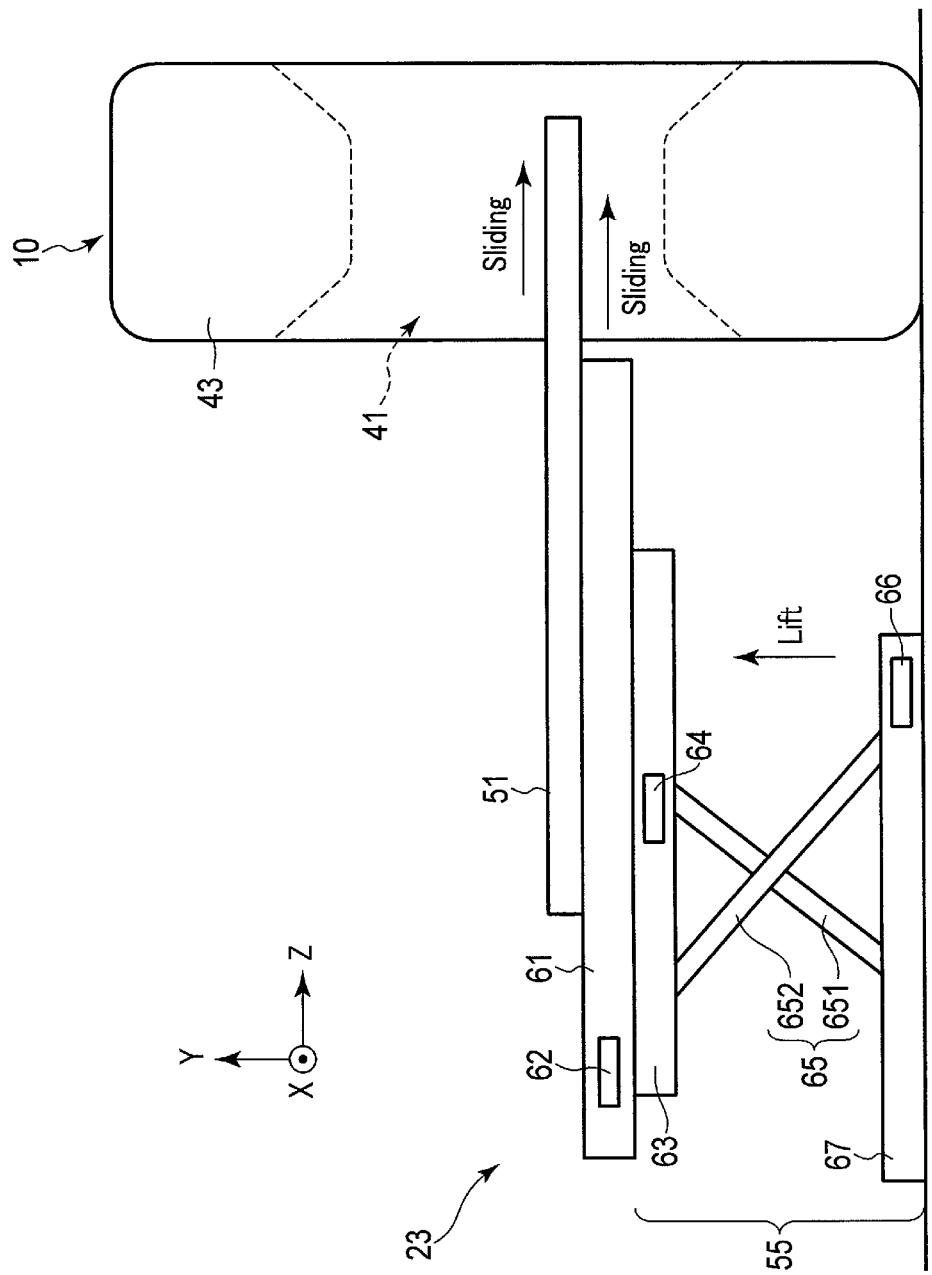
FIG. 3 is a view schematically showing a side surface of a bed according to this embodiment.

FIG. 3 is a view schematically showing a side surface of the bed 23 according to this embodiment. Referring to FIG. 3, an illustration of the housing of the bed 23 is omitted. As shown in FIG. 3, the upper frame 61 supports the top 51 so as to allow it to slide in the Z direction parallel to the long axis direction of the top 51. The upper frame 61 may have any structure as long as it allows the top 51 to slide. For example, the upper frame 61 has a frame-like frame (not shown) that guides the sliding of the top 51 in the Z direction. The upper frame 61 is provided with a top driving controller 62 that generates power for making the top 51 slide in the Z direction. The top driving controller 62 is implemented by an existing motor such as a servo motor. The top driving controller 62 operates under the control of the gantry control circuitry 33.

As shown in FIG. 3, the support base 55 is installed on the floor surface. The support base 55 moves the upper frame 61 up and down in the Y direction and back and forth in the Z direction. More specifically, the support base 55 includes a lower frame 63, an X link 65, and a mount 67. The lower frame 63 supports the upper frame 61 so as to allow it to slide in the Z direction parallel to the long axis direction of the upper frame 61. The lower frame 63 may have any structure as long as it allows the upper frame 61 to slide. For example, the lower frame 63 has a frame-like frame that guides the sliding of the upper frame 61 in the Z direction. The lower frame 63 is provided with a frame driving controller 64 that generates power for making the upper frame 61 slide in the Z direction. The frame driving controller 64 is implemented by an existing motor such as a servo motor. The frame driving controller 64 operates under the control of the gantry control circuitry 33.

As shown in FIG. 3, the support base 55 is installed on the floor surface. The support base 55 has a support structure that can move the lower frame 63 up and down in the Y direction while approaching or separating from the gantry 10. For example, the support base 55 includes the X link 65 and the mount 67. The X link 65 is connected to the lower frame 63 and the mount 67. The mount 67 is provided with a lift/lower driving controller 66 that generates power for causing the X link 65 to lift or lower the lower frame 63 in the Y direction. The lift/lower driving controller 66 is implemented by an existing motor such as a servo motor. The lift/lower driving controller 66 operates under the control of the gantry control circuitry 33.

As shown in FIG. 3, the X link 65 includes a pair of a movable link 651 and a fixed link 652 that are pivotally supported in an X form. The movable link 651 and the fixed link 652 are rotatably centered and provided on the pivot shaft. The movable link 651 and the fixed link 652 are formed from a pair of metal plates, each having a plate-like shape, with almost the same length. One end of the fixed link 652 is fixed to the mount 67. The other end of the fixed link 652 is fixed to the lower frame 63. One end of the movable link 651 is supported on the mount 67 so as to be slidable in the Z direction. The other end of the movable link 651 is supported on the lower frame 63 so as to be slidable in the Z direction. The lift/lower driving controller 66 reduces the interval between the movable link 651 and the fixed link 652 in the Z direction to make the lower frame 63 approach the gantry 10 while lifting. The lift/lower driving controller 66 increases the interval between the movable link 651 and the fixed link 652 in the Z direction to make the lower frame 63 separate from the gantry 10 while lowering.

Figure 4:
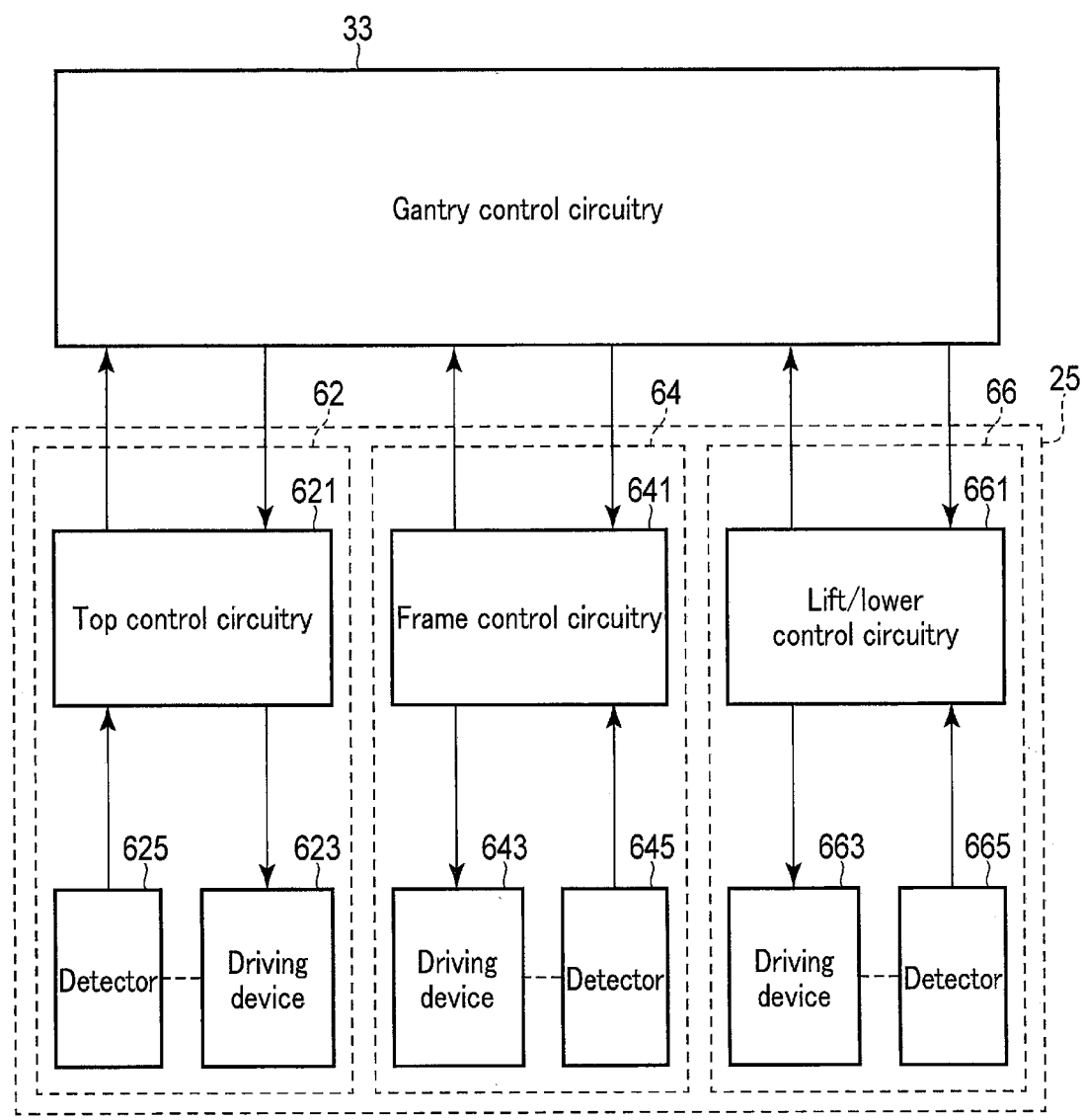
FIG. 4 is a block diagram showing an example of the arrangement of gantry control circuitry and a bed driving system according to this embodiment.

FIG. 4 is a block diagram showing an example of the arrangement of the gantry control circuitry 33 and the bed driving device 25 according to this embodiment. As shown in FIG. 4, the bed driving device 25 includes the top driving controller 62, the frame driving controller 64, and the lift/lower driving controller 66. The gantry control circuitry 33 controls the top driving controller 62, the frame driving controller 64, and the lift/lower driving controller 66 to move the top 51 to a desired position.

The top driving controller 62 is provided on, for example, the upper frame 61. The top driving controller 62 causes the top 51 to slide upon receiving an operation instruction signal from the gantry control circuitry 33. More specifically, the top driving controller 62 includes top control circuitry 621, a driving device 623, and a detector 625. The top control circuitry 621 is a servo amplifier that receives an operation instruction signal from the gantry control circuitry 33 and supplies power corresponding to the operation instruction signal to the driving device 623. Upon receiving the power from the top control circuitry 621, the driving device 623 drives to actuate the upper frame 61, to which the top 51 is connected, to cause the top 51 to slide. More specifically, the driving device 623 is a motor that generates power by rotating the drive shaft. The detector 625 is a position detector such as a rotary encoder provided on the drive shaft of the driving device 623.

The frame driving controller 64 is provided on, for example, the lower frame 63. Upon receiving an operation instruction signal from the gantry control circuitry 33, the frame driving controller 64 causes the upper frame 61 to slide. More specifically, the frame driving controller 64 includes frame control circuitry 641, a driving device 643, and a detector 645. The frame control circuitry 641 is a servo amplifier that receives an operation instruction signal from the gantry control circuitry 33 and supplies power corresponding to the operation instruction signal to the driving device 643. Upon receiving power from the frame control circuitry 641, the driving device 643 drives to actuate the lower frame 63, to which the upper frame 61 is connected, to cause the upper frame 61 to slide. More specifically, the driving device 643 is a motor that generates power by rotating the drive shaft. The detector 645 is a position detector such as a rotary encoder provided on the drive shaft of the driving device 643.

The lift/lower driving controller 66 is provided on, for example, the support base 55. Upon receiving an operation instruction signal from the gantry control circuitry 33, the lift/lower driving controller 66 actuates the X link 65 to lift/lower (move up and down) the top 51, the upper frame 61, and the lower frame 63. More specifically, the lift/lower driving controller 66 includes lift/lower control circuitry 661, driving device 663, and a detector 665. The lift/lower control circuitry 661 is a servo amplifier that receives an operation instruction signal from the gantry control circuitry 33 and supplies power corresponding to the operation instruction signal to the driving device 663. Upon receiving the power from the lift/lower control circuitry 661, the driving device 663 drives to actuate the X link 65, to which the top 51, the upper frame 61, and the lower frame 63 are connected, to lift/lower them. The detector 665 is a position detector such as a rotary encoder provided on the drive shaft of the driving device 663.

The X-ray computed tomography apparatus 1 according to this embodiment will be described in detail below.

Figure 5:
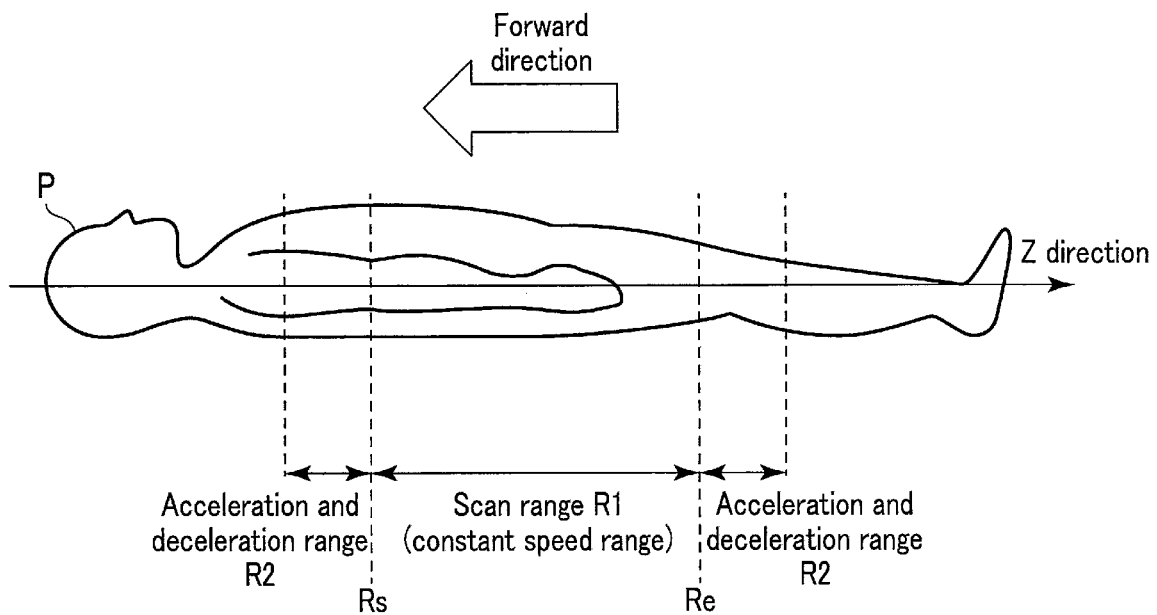
FIG. 5 is a view showing the relationship between a scan range in helical scanning and the speed of the top according to this embodiment.

FIG. 5 is a view showing the relationship between a scan range R1 of helical scanning and the speed of the top 51. As shown in FIG. 5, the scan range R1 is set in an arbitrary range of the object P in the Z direction. In a helical scan, the gantry control circuitry 33 causes the top 51 to slide at a set speed while the gantry 10 scans the scan range R1 with X-rays. One end of the two ends of the scan range R1 in the Z direction which corresponds to the rear side end portion in the forward direction is called a scan starting end Rs, and the other end corresponding to the front side end portion in the forward direction is called a scan finishing end Re. In addition, a helical scan according to this embodiment is performed either in the standard speed mode of making the top 51 slide in the scan range R1 at standard speed or in the high speed mode of making the top 51 slide at high speed relative to the standard speed. The standard speed is set to, for example, about 200 mm/s. The high speed is set to, for example, about 400 mm/s.

It is necessary to accelerate the top 51 on the front side of the scan range R1 in the forward direction to cause the top 51 to slide at the set speed in the scan range R1. In addition, in order to stop the top after the end of a scan in the scan range R1, it is necessary to decelerate the top on the rear side of the scan range R1 in the forward direction. Note that although the forward direction in FIG. 5 is defined as a direction from the head portion to the left portion of the object P, this direction may be defined as a direction from the leg portion to the head portion. In this embodiment, the ranges in which the top 51 slides at a constant speed, that is, the scan range R1 is called a constant speed range and a range R2 in which the top 51 is accelerated or decelerated is called an acceleration/deceleration range.

Note that helical scans according to this embodiment include a type (to be referred to as a one-way helical scan hereinafter) that moves the top 51 from one end to the other end of the scan range R1 in one direction and a type (to be referred to as a reciprocal helical scan hereinafter) that reciprocally moves the top 51 between the two ends of the scan range R1. Both the types of helical scans can be applied to this embodiment. In the following description, however, for the sake of simplicity, a helical scan is a one-way helical scan unless otherwise specified.

As described above, the top 51 and the upper frame 61 supporting the top 51 independently slide in the Z direction. However, the upper frame 61 is a portion that is driven when the object P is positioned, and does not usually operate during a helical scan. Accordingly, the following problems arise in a helical scan in the high speed mode.

Figure 6:
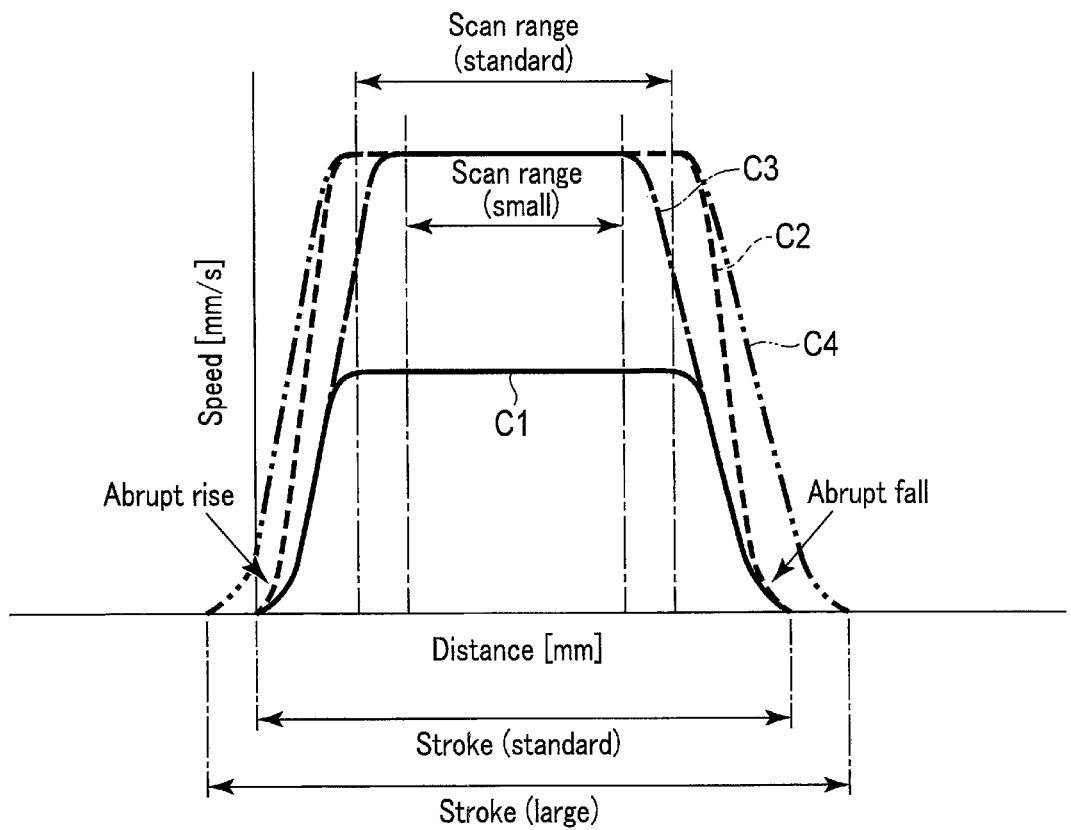
FIG. 6 is a graph showing the relationship between the speed and the slide distance of the top in each of a standard speed mode and a high speed mode while an upper frame is fixed.

FIG. 6 is a graph showing the relationship between the speed and the slide distance of the top 51 in each of the standard speed mode and the high speed mode while the upper frame 61 is fixed. The ordinate of the graph of FIG. 6 defines the speed [mm/s] of the top 51, and the abscissa defines the slide distance [mm] of the top 51 in the Z direction. The origin of the slide distance axis is defined at the moving start position of the top 51 in the standard mode.

As indicated by a curve C1 in FIG. 6, in the standard speed mode, the top 51 slides at the standard speed over a scan range having a standard size. In the standard speed mode, the top 51 is only required to be accelerated to the standard speed in an acceleration and deceleration range, and hence there is no need to rapidly increase the speed of the top 51 in the acceleration and deceleration range. The distance (stroke) from the start of movement of the top 51 to the stoppage of movement is a standard distance. As indicated by a curve C2 in FIG. 6, in the high speed mode with a scan range having a standard size, it is necessary to rapidly increase the speed of the top 51 in an acceleration and deceleration range as compared with the standard speed mode. Rapidly increasing the speed of the top 51 will increase the load on the object P. As indicated by a curve C3 in FIG. 6, when a speed change in the acceleration and deceleration range in the high speed mode is adjusted to that in the standard mode, it is necessary to reduce the scan range. In addition, as indicated by a curve C4 in FIG. 6, when a speed change in the acceleration and deceleration range in the high speed mode is adjusted to that in the standard mode and the scan range is set to the standard size, it is inevitably necessary to increase the distance (stroke) between the start of sliding of the top 51 and the stoppage of sliding. This makes it necessary to increase the length of the bed 23 in the Z direction.

The gantry control circuitry 33 according to this embodiment synchronously controls the top driving controller 62 and the frame driving controller 64 so as to execute an operation (to be referred to as a start auxiliary operation hereinafter) for accelerating the top 51 to a set speed and an operation (to be referred to as a stop auxiliary operation hereinafter) for stopping the top 51. When performing the start auxiliary operation, the gantry control circuitry 33 positions the upper frame 61 at the moving start position decided based on scan conditions, and then controls the frame driving controller 64 to accelerate the upper frame 61 along the forward direction before moving the top 51 when starting to move the object P in a scan. After the lapse of a predetermined time since the start of acceleration control on the upper frame 61 by the frame driving controller 64, the gantry control circuitry 33 controls the top driving controller 62 to accelerate the top 51 to a set speed along the forward direction. More specifically, after retracting the top 51 and the upper frame 61 from the initial position to the moving start position on the opposite side in the forward direction, the gantry control circuitry 33 accelerates the upper frame 61 along the forward direction before moving the top 51, and accelerates the top 51 to a set speed when decelerating the upper frame 61. This start auxiliary operation makes it possible to accelerate the top 51 to the set speed within a limited space while reducing the load on the object P.

When performing a stop auxiliary operation, the gantry control circuitry 33 controls the frame driving controller 64 to accelerate the upper frame 61 along the forward direction at the time of decelerating the top 51. After the lapse of a predetermined time since the start of acceleration control on the upper frame 61 by the frame driving controller 64, the gantry control circuitry 33 controls the top driving controller 62 to stop the top 51. More specifically, the gantry control circuitry 33 decelerates the top 51 along the forward direction, accelerates the upper frame 61 in the forward direction at the time of decelerating the top 51, and stops the top 51 while decelerating the upper frame 61. Thereafter, the gantry control circuitry 33 stops the upper frame 61. This stop auxiliary operation makes it possible to stop the top 51 within a limited space while reducing the load on the object P.

A bed operation mode of performing these start auxiliary operation and stop auxiliary operation will be called a perceived speed reduction mode, and a bed operation mode without such start auxiliary operation and stop auxiliary operation will be called a standard operation mode.

The details of the X-ray computed tomography apparatus 1 according to this embodiment will be described next. The operation of the X-ray computed tomography apparatus 1 according to this embodiment is divided into a scan planning step and a helical scanning step. In the scan planning step, a bed operation mode is set. In the helical scanning step, a helical scan corresponding to the bed operation mode is performed.

Figure 7:
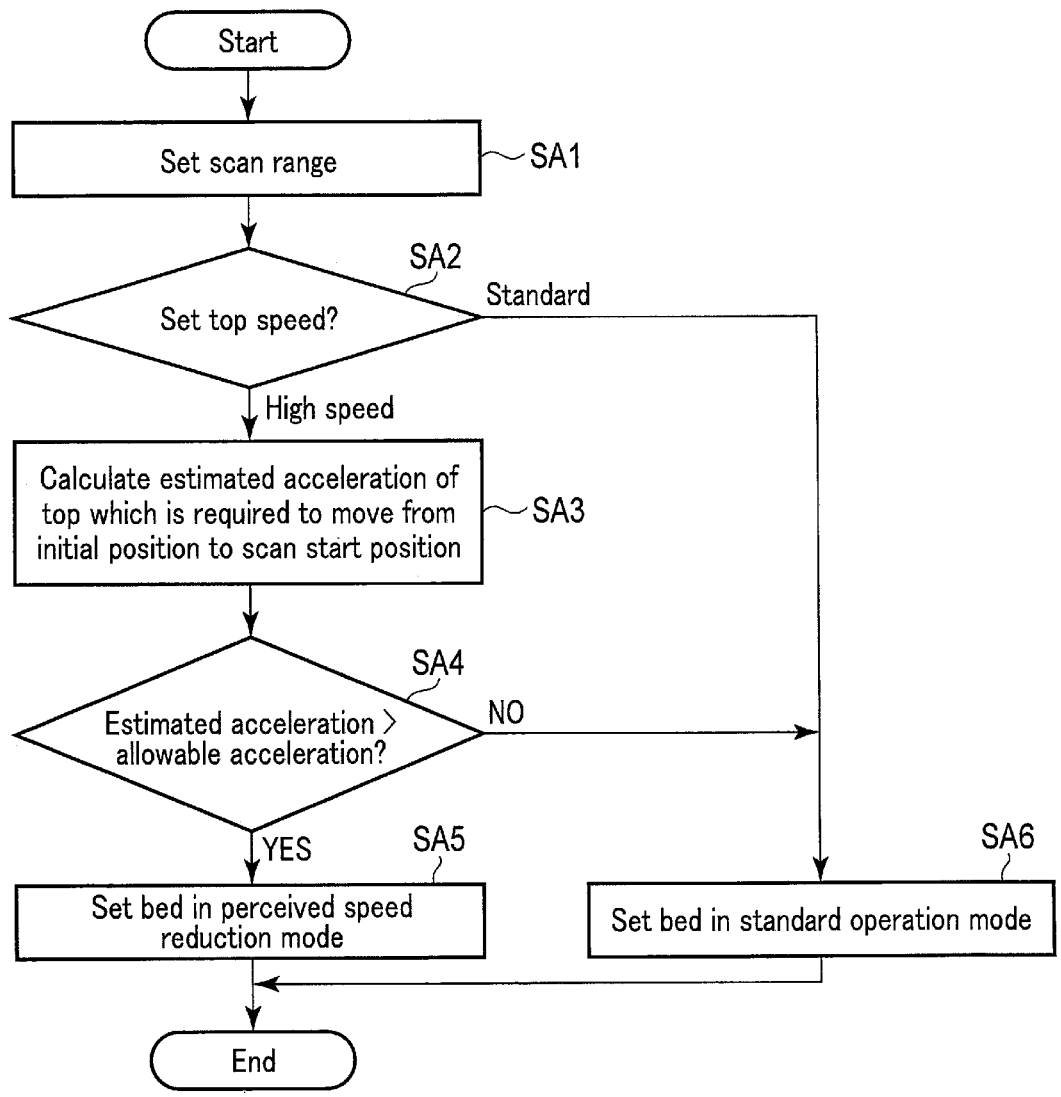
FIG. 7 is a flowchart showing a processing procedure of a scan planning function implemented by processing circuitry according to this embodiment.

FIG. 7 is a flowchart showing a processing procedure of the scan planning function 117 implemented by the processing circuitry 101 according to this embodiment. With the scan planning function 117, the processing circuitry 101 sets a bed operation mode to the perceived speed reduction mode or the standard operation mode based on scan conditions. The scan conditions include the scan range of a helical scan and the set speed of the top 51. The scan planning function 117 will be described in detail below.

As shown in FIG. 7, the processing circuitry 101 sets the scan range of a helical scan (step SA1). In step SA1, the processing circuitry 101 sets a scan range in accordance with an instruction issued by the user via the input device 105. For example, before step SA1, the gantry control circuitry 33 controls the X-ray high voltage device 17, the data acquisition circuitry 19, the gantry driving device 21, and the bed driving device 25 to execute a positioning scan targeted to the object P. A positioning scan is a technique of scanning a predetermined range of the object P while making the top 51 slide in the Z direction, with the rotational angle of the X-ray tube 13 being fixed. The processing circuitry 101 generates a scanogram concerning the object P based on the raw data acquired by the positioning scan. The display device 103 displays the scanogram.

Figure 8:
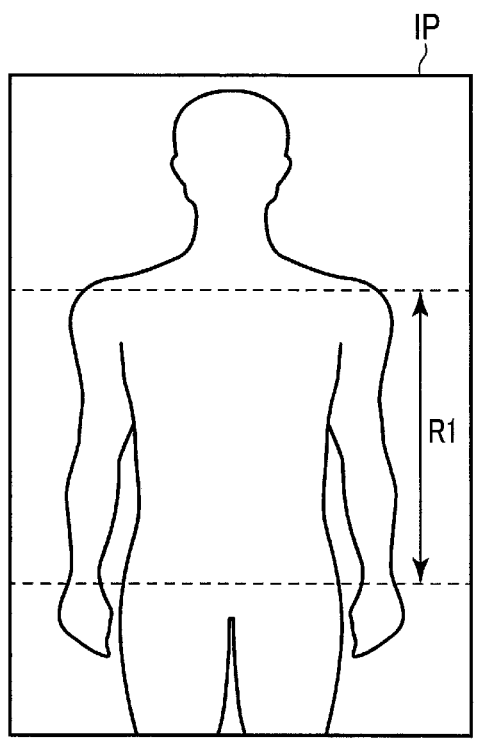
FIG. 8 is a view showing an example of a scanogram displayed in step SA1 in FIG. 7.

FIG. 8 is a view showing an example of a scanogram IP displayed in step SA1. As shown in FIG. 8, the scanogram IP is a projection image of the object P over a predetermined range. The user designates the scan range R1 on the scanogram by operating the input device. The processing circuitry 101 sets the scan range R1 in the designated range. The scan range R1 according to this embodiment may be set in any range. Note that the scanogram IP is not limited to an image in the AP (Anterior-Posterior) direction, and an image in an LR (Left-Right) direction or arbitrary imaging direction may be used as long as it allows the setting of the scan range R1.

Upon executing step SA1, the processing circuitry 101 determines whether the set speed of the top 51 in the helical scan is the standard speed or the high speed (step SA2). The set speed may be set at the time of step SA2 or before step SA2. A set speed may be arbitrarily selected in accordance with an instruction issued via the input device 105 by the user. Note that set speeds to be set are not limited to the two types of speeds, namely the standard speed and the high speed. For example, three types or more of speeds may be prepared, and any of the speeds may be set, and an arbitrary speed may be set. In this case, a speed higher than the threshold is determined as a high speed, and a speed lower than the threshold is determined as the standard speed.

Upon determining that the set speed of the top 51 is the high speed (YES in step SA2), the processing circuitry 101 calculates an estimated acceleration required for the top 51 to move from the initial position to the scan start position (step SA3).

Figure 9:
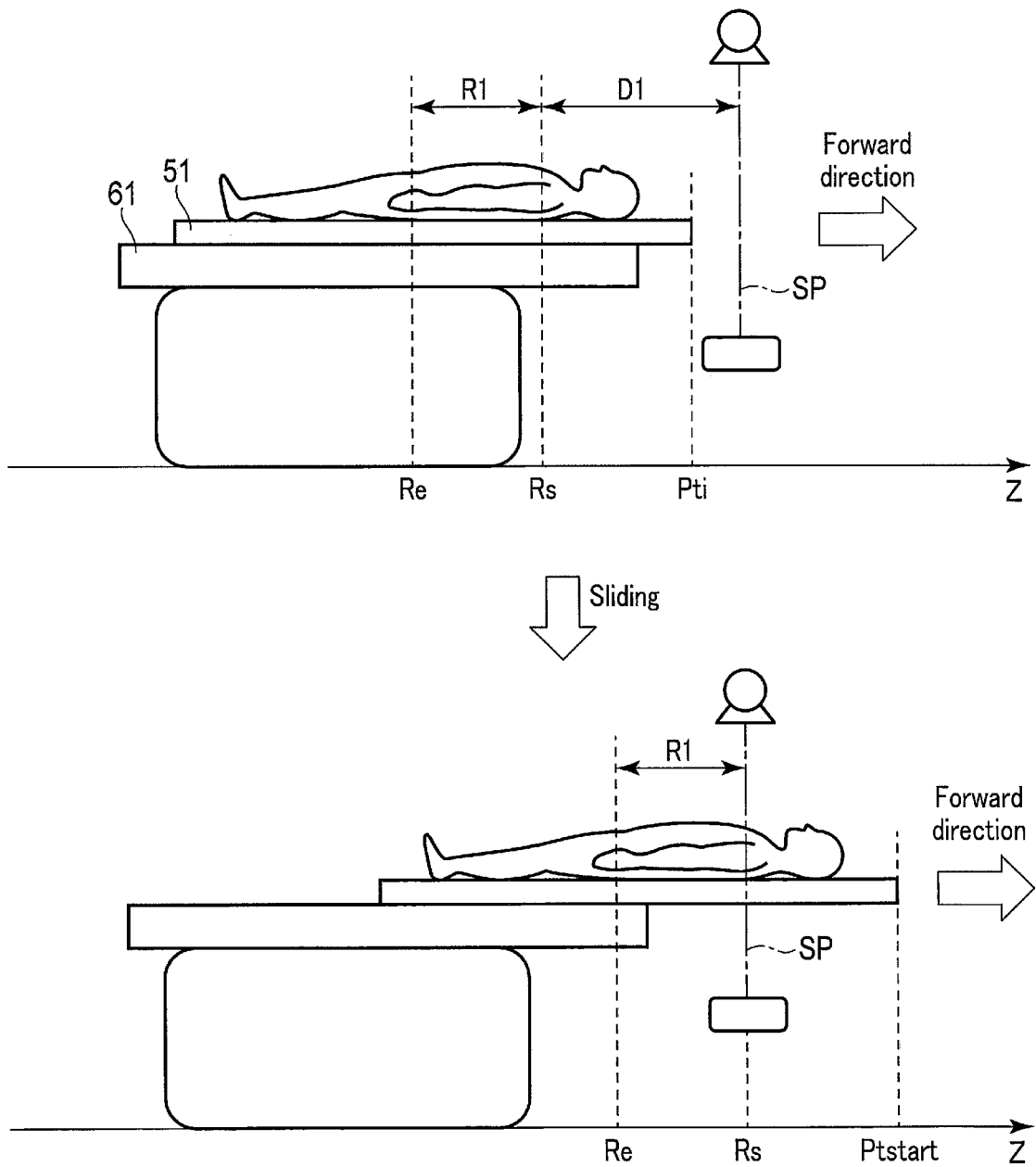
FIG. 9 is a view showing the positional relationship between the initial position and the scan start position of the top according to this embodiment.

FIG. 9 is a view showing the positional relationship between an initial position Pti and a scan start position Ptstart of the top 51. As shown in FIG. 9, the initial position Pti is defined at the position of the top at the time point of step SA3. The position Ptstart is defined at the position of the top when the scan start end Rs intersects with a scan plane SP. The position of the top indicates the position of a reference point on the top 51 in the Z direction. The reference position of the top 51 may be set in any portion. For example, the reference point is defined at the rear side end portion of the top 51 in the forward direction. The scan plane SP is defined at a plane connecting the focus of the X-ray tube 13 to a central array of the X-ray detector 15. Note that the position Ptstart is not limited to this and may be defined at the position of the top when the scan start end Rs is located at a position offset from the scan plane SP by a predetermined distance. Typically, after the end of the positioning scan, the top 51 is moved to the moving start position (default moving start position) in the standard mode. In this case, the initial position Pti coincides with the moving start position in the standard mode. Note that after the end of the positioning scan, the top 51 need not always be moved to the moving start position in the standard mode, and the initial position Pti may be at an arbitrary position.

More specifically, in step SA3, first of all, the processing circuitry 101 measures a distance D1 from the scan start end Rs at the initial position Pti to the scan plane SP based on the position of the scan range R1 in the Z direction and the position of the top (default moving start position) at the initial position Pti. Based on the distance D1 and the set speed of the top 51, the processing circuitry 101 then calculates an acceleration (estimated acceleration) required for the speed of the top to increase from 0 to the set speed while the top 51 slides by the distance D1. The required acceleration may be constant or may gradually change near the moving start time and the set speed reaching time and may rapidly change between the times.

Upon executing step SA3, the processing circuitry 101 determines whether the estimated acceleration calculated in step SA3 is larger than the allowable acceleration (step SA4). The allowable acceleration is set to an acceleration allowed by the object P. The allowable acceleration may be set to an arbitrary value by the user via the input device 105. When the estimated acceleration is larger than the allowable acceleration, it indicates that the load on the object P is relatively large, and the object P cannot tolerate the estimated acceleration. When the estimated acceleration is smaller than the allowable acceleration, it indicates that the load on the object P is relatively small, and the object P can tolerate the estimated acceleration.

Accordingly, upon determining in step SA4 that the estimated acceleration is larger than the allowable acceleration (YES in step SA4), the processing circuitry 101 sets a bed operation mode to the perceived speed reduction mode for reducing the load by reducing the speed perceived by the object P (step SA5). That is, the processing circuitry 101 determines, based on comparison between the estimated acceleration and the allowable acceleration, whether to set the bed operation mode to the perceived speed reduction mode or the standard operation mode.

Upon determining in step SA4 that the estimated acceleration is smaller than the perceived speed (NO in step SA4) or the set speed of the top is the standard speed (standard in step SA2), the processing circuitry 101 sets the bed operation mode to the standard speed mode (step SA6).

Upon executing step SA5 or step SA6, the processing circuitry 101 terminates the scan planning function 117. When the scan planning function 117 makes a scan plan, a helical scan is performed based on the scan plan. For example, when preparations are made for the helical scan and the user presses a confirmation button by operating the input device 105, the helical scan is started. An example of the operation of the X-ray computed tomography apparatus 1 in a helical scan in the perceived speed reduction mode will be described below.

Figure 10:
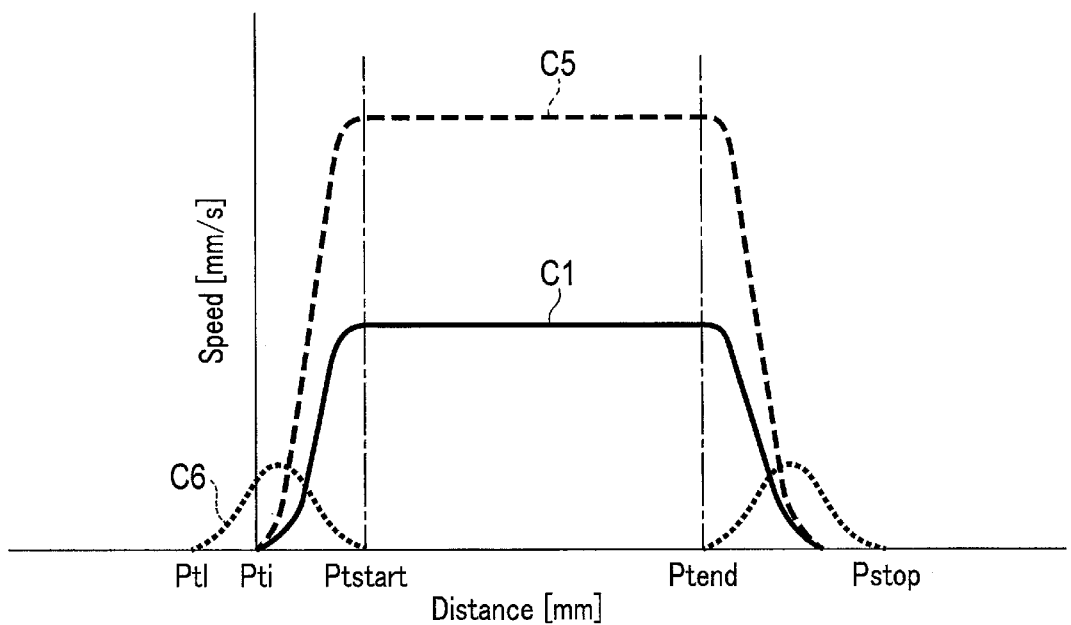
FIG. 10 is a graph showing the relationship between the individual speeds and slide distances of the top and the upper frame in each of the standard speed mode and the high speed mode according to this embodiment.
Figure 11:
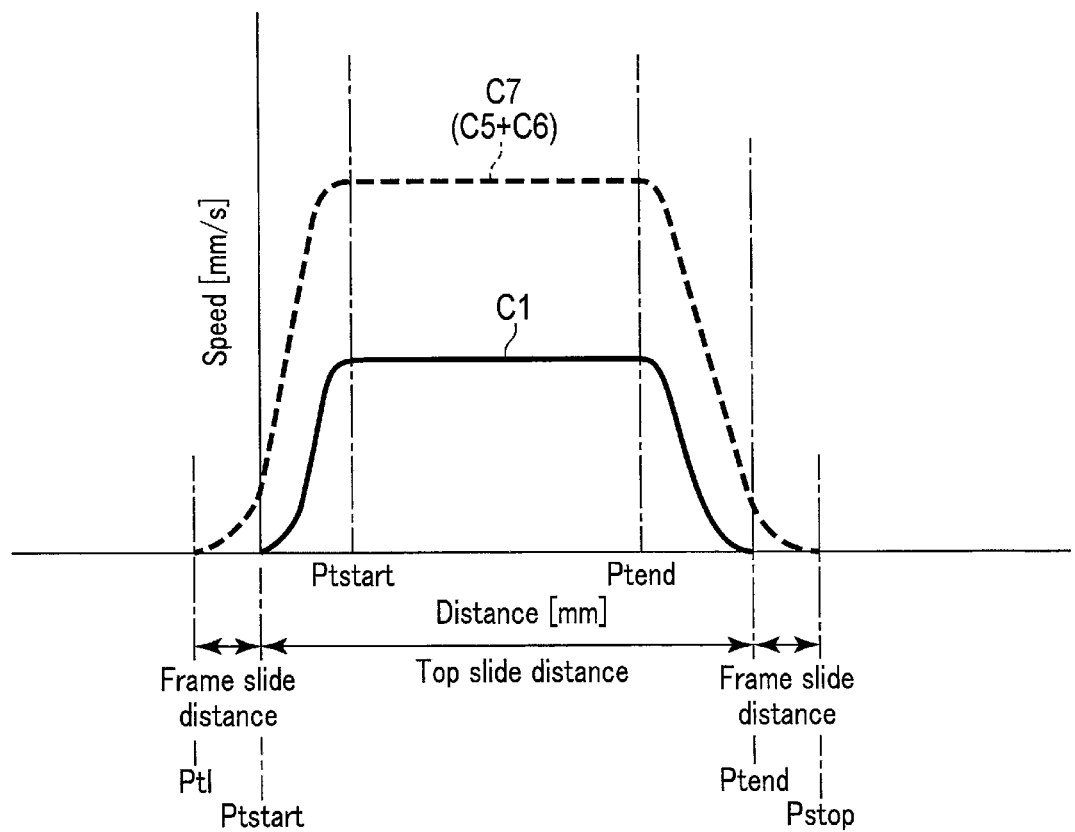
FIG. 11 is a view showing the relationship between the sum of the speeds and the slide distances of the top and the upper frame in each of the standard speed mode and the high speed mode.

FIG. 10 is a graph showing the relationship between the individual speeds and the slide distances of the top 51 and the upper frame 61 in each of the standard speed mode and the high speed mode. FIG. 11 is a graph showing the relationship between the total speed of the top 51 and the upper frame 61 and slide distance in each of the standard speed mode and the high speed mode. Referring to FIGS. 10 and 11, the ordinate defines speed [mm/s], and the abscissa defines slide distance [mm]. The origin of the abscissa is defined at the moving start position of the top 51. Note that in the standard speed mode, the upper frame 61 is fixed to the lower frame 63, and only the top 51 is actuated. In the high speed mode, the upper frame 61 and the top 51 are individually actuated.

A curve C1 in FIG. 10 indicates the relationship between the individual speed and slide distance of the top 51 in the standard speed mode as in C1 of FIG. 6. A curve C5 in FIG. 10 indicates the relationship between the individual speed and slide distance of the top 51 in the high speed mode. A curve C6 in FIG. 10 indicates the relationship between the individual speed and slide distance of the upper frame 61 in the high speed mode. A curve C7 in FIG. 11 indicates the relationship between the apparent speed and slide distance of the top 51 in the high speed mode. The apparent speed of the top 51 is the sum of the relative speed of the top 51 with respect to the upper frame 61 and the relative speed of the upper frame 61 with respect to the lower frame 63. In other words, the apparent speed of the top 51 is the relative speed perceived by the object P.

In a helical scan in the high speed mode using the perceived speed reduction mode, a start auxiliary operation, a scan operation, and a stop auxiliary operation are performed in the order named. The start auxiliary operation and the scan operation will be described first.

Figure 12:
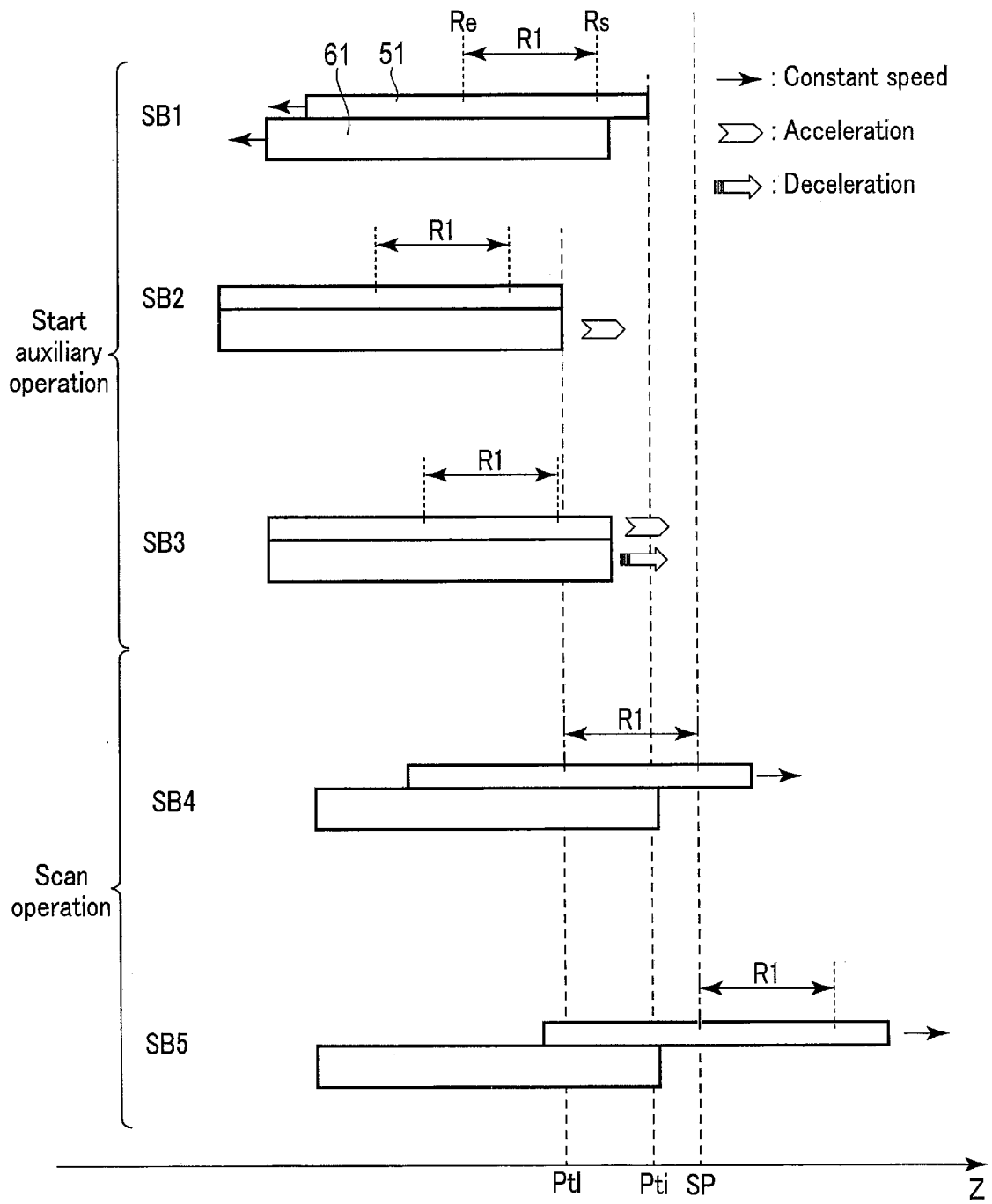
FIG. 12 is a view schematically showing the operations of the top and the upper frame in a start auxiliary operation and a scan operation in the high speed mode according to this embodiment.

FIG. 12 is a view schematically showing the operations of the top 51 and the upper frame 61 in the start auxiliary operation and the scan operation. As shown in FIG. 12, at the start time of the start auxiliary operation, the top 51 is located at the initial position Pti. First of all, the gantry control circuitry 33 controls the top driving controller 62 and the frame driving controller 64 to retract the top 51 and the upper frame 61 to a predetermined moving start position Ptl (step SB1). The position Ptl is located closer to the opposite side (the front side in the forward direction) in the forward direction of the top 51 in a helical scan than the moving start position in the standard mode (default moving start position). The position Ptl is typically set to the moving limit position on the front side in the forward direction. Note that referring to FIG. 12, the position Ptl of the top 51 is the same as that of the upper frame 61 in the Z direction. However, they may be set at different positions.

Before accelerating the top 51, the gantry control circuitry 33 controls the top driving controller 62 and the frame driving controller 64 to accelerate the upper frame 61 in the forward direction while stopping the top 51 relative to the upper frame 61 (step SB2). The maximum speed of the upper frame 61 is lower than the set high speed and the set standard speed of the top 51, as shown in FIGS. 10 and 11. If, for example, the set high speed is 400 mm/s and the set standard speed is 200 mm/s, the maximum speed of the upper frame 61 is preferably set to about 100 mm/s.

The gantry control circuitry 33 controls the top driving controller 62 to accelerate the top 51 up to the set speed along the forward direction after the lapse of a predetermined time since the start of acceleration control on the upper frame 61 by the frame driving controller 64 (step S3). The predetermined time is set to, for example, a time from the start of acceleration of the upper frame 61 to a time point within the period of deceleration after the acceleration.

More specifically, when the speed of the upper frame 61 reaches the maximum speed, the gantry control circuitry 33 controls the top driving controller 62 and the frame driving controller 64 to accelerate the top 51 relative to the upper frame 61 in the forward direction at the time of decelerating the upper frame 61 while decelerating the upper frame 61. Accelerating the top 51 at the time of moving the upper frame 61 in the same direction can reduce the perceived speed of the object P which originates from the sliding of the top 51. As shown in FIGS. 10 and 11, the gantry control circuitry 33 decelerates and stops the upper frame 61 while accelerating the top 51. The gantry control circuitry 33 stops the upper frame 61 at a position where the upper frame 61 is not included in the opening 41. Typically, the upper frame 61 is stopped near the gantry 10 in the −Z direction of the gantry 10. This can prevent the occurrence of artifacts accompanying the scanning of the upper frame 61.

The gantry control circuitry 33 accelerates the apparent speed of the top 51 to the set high speed by the time when the position of the top reaches the position Ptstart, that is, the scan start end Rs reaches the scan plane SP. In this case, in order to make the apparent speed of the top 51 smoothly reach the set high speed, the gantry control circuitry 33 accelerates the top 51 while decelerates the upper frame 61.

In the above manner, the gantry control circuitry 33 completes the start auxiliary operation. AS described above, in the start auxiliary operation, upon retracting the top 51 and the upper frame 61 from the initial position Pti to the position Ptl, the gantry control circuitry 33 accelerates at first the upper frame 61, and then accelerates the top 51 at the time of decelerating the upper frame 61. This can increase the slide distance of the top 51 relative to the upper frame 61 until the top 51 reaches the set high speed, thus reducing the acceleration of the top 51 as compared with the case in which the upper frame 61 is fixed. It is, therefore, possible to reduce the load on the object P caused by acceleration.

According to the above description, in a start auxiliary operation, the top 51 and upper frame 61 are retracted from the initial position Pti to the position Ptl. However, this embodiment is not limited to this. For example, in a start auxiliary operation, at first, the gantry control circuitry 33 may retract the top 51 and the upper frame 61 from the initial position Pti to a moving start position closer to the scan plane SP than the position Ptl. The retraction distance from the initial position Pti to a moving start position, that is, a moving start position, is calculated by the processing circuitry 101 with the scan planning function 117.

For example, the processing circuitry 101 decides a moving start position based on the position Ptstart and a set speed. More specifically, the processing circuitry 101 calculates a retraction distance based on the distance from the initial position Pti to the position Ptstart and an allowable acceleration. More specifically, the processing circuitry 101 calculates a retraction distance such that an acceleration at which the top 51 slides from a moving start position to the scan start position Ptstart coincides with an allowable acceleration. A position separated from the initial position Pti by the retraction distance is set as a moving start position.

According to this embodiment, it is possible to reduce the retraction distance as compared with the case in which the top 51 and the upper frame 61 are retracted to the moving limit position, and hence it is possible to improve the throughput of a helical scan while reducing the load on the object P accompanying acceleration.

Note that in the above start auxiliary operation, it is assumed that the initial position Pti is not located at the moving start position. However, this embodiment is not limited to this. For example, the top 51 is located at a moving start position such as a moving limit position under the control of the gantry control circuitry 33 when the X-ray computed tomography apparatus 1 is started up or the next patient is ready for examination. In this case, the retraction operation in step SB1 is not necessary.

As shown in FIG. 12, when the position of the top reaches the position Ptstart, the gantry control circuitry 33 controls the bed driving device 25 to constantly move the top 51 at a set high speed and, at the same time, synchronously controls the X-ray high voltage device 17, the data acquisition circuitry 19, and the gantry driving device 21 to scan the object P over the scan range R1 (step SB4). When the position of the top reaches a scan end position Ptend, that is, when the scan finishing end Re reaches the scan plane SP, the gantry control circuitry 33 synchronously controls the X-ray high voltage device 17, the data acquisition circuitry 19, and the gantry driving device 21 to end the scan (step SB5).

When the position of the top reaches the position Ptend, the gantry control circuitry 33 starts a stop auxiliary operation.

FIG. 13 is a view schematically showing the operations of the top 51 and the upper frame 61 in a stop auxiliary operation. As shown in FIG. 13, when the scan ends, the position of the top is located at the position Ptend, and the upper frame 61 is located at a scan end position Pfe. Because the upper frame 61 does not move at the time of a scan, the position Pfe is the same as the stop position of the upper frame 61 in a start auxiliary position. That is, the position Pfe is located in front of the opening 41. As shown in FIGS. 10, 11, and 13, the gantry control circuitry 33 accelerates and decelerates the upper frame 61 in the same direction as the forward direction of the top 51 so as to gradually reduce the apparent moving speed of the top 51 to 0 by the time when the position of the top reaches a stop position Pstop.

More specifically, first of all, when the position of the top reaches the position Ptend, the gantry control circuitry 33 controls the top driving controller 62 and the frame driving controller 64 to accelerate the upper frame 61 in the forward direction while decelerating the top 51 along the same direction (step SC1). In this case, the upper frame 61 enters the opening 41. This operation is allowed. This is because the scan is completed, and hence there is no need to worry about artifacts accompanying the scan on the upper frame 61.

Subsequently, after the lapse of a predetermined time since the start of acceleration control on the upper frame 61 by the frame driving controller 64, the gantry control circuitry 33 controls the top driving controller 62 to stop the top 51 (step SC2). The predetermined time is set to, for example, a time from the start of acceleration of the upper frame 61 to a time point within the period of deceleration after the acceleration.

More specifically, when the upper frame 61 reaches a predetermined speed, the gantry control circuitry 33 controls the top driving controller 62 and the frame driving controller 64 to decelerate the upper frame 61 and stop the top 51 relative to the upper frame 61 during the deceleration of the upper frame 61. The upper frame 61 supporting the top 51 has slid at the time point of step SC2, and hence the apparent position of the top 51 has moved. The gantry control circuitry 33 controls the frame driving controller 64 to gradually stop the upper frame 61 so as to stop the position of the top at the position Pstop. This also stops the apparent position of the top 51.

In the above manner, the stop auxiliary operation by the gantry control circuitry 33 is completed. As described above, in the stop auxiliary operation, after the position of the top reaches the position Ptend, the gantry control circuitry 33 accelerates the upper frame 61 in the forward direction while decelerating the top 51 along the same direction, stops the top 51 relative to the upper frame 61 at the time of decelerating the upper frame 61, and stops the upper frame 61. This makes it possible to increase the slide distance of the top 51 relative to the upper frame 61 until the top 51 stops at an apparent position. This can reduce the deceleration of the top 51 (acceleration in the −Z direction) as compared with a case in which the upper frame 61 is fixed. It is, therefore, possible to reduce the load on the object P caused by deceleration.

An example of the operation of the X-ray computed tomography apparatus 1 in a helical scan in the perceived speed reduction mode has been described above.

Note that a helical scan according to this embodiment is not limited to only a one-way helical scan, and can be applied to a reciprocal helical scan. In this case, for example, in a forward scan, the gantry control circuitry 33 performs a start auxiliary operation when accelerating the position of the top to the front side end portion of a scan range in the forward direction (for example, the +Z direction). In addition, upon making the position of the top pass through to the rear side end portion of the scan range in the forward direction, the gantry control circuitry 33 performs a stop auxiliary operation when stopping the top 51 at a turning point. In a backward scan as well, the gantry control circuitry 33 performs a start auxiliary operation when accelerating the position of the top to the front side end portion of the scan range in the forward direction (for example, the −Z direction). Upon making the position of the top pass through to the rear side end portion of the scan range in the forward direction, the gantry control circuitry 33 performs a stop auxiliary operation when stopping the top 51 at the turning point.

In a reciprocal helical scan as well, this makes it possible to reduce the load on the object P accompanying acceleration/deceleration.

The perceived speed reduction mode according to this embodiment can also be applied to an emergency stop operation for the bed 23. The operations of the top 51 and the upper frame 61 in an emergency stop operation will be described below. Note that an emergency stop operation indicates an operation of emergently stopping the operation of the bed 23 because of a mechanical factor concerning, for example, the bed 23, the gantry 10, and the X-ray computed tomography apparatus 1. A mechanical factor indicates, for example, a power failure. In an emergency stop operation, the top 51 may be stopped at an arbitrary position in many cases.

Figure 14:
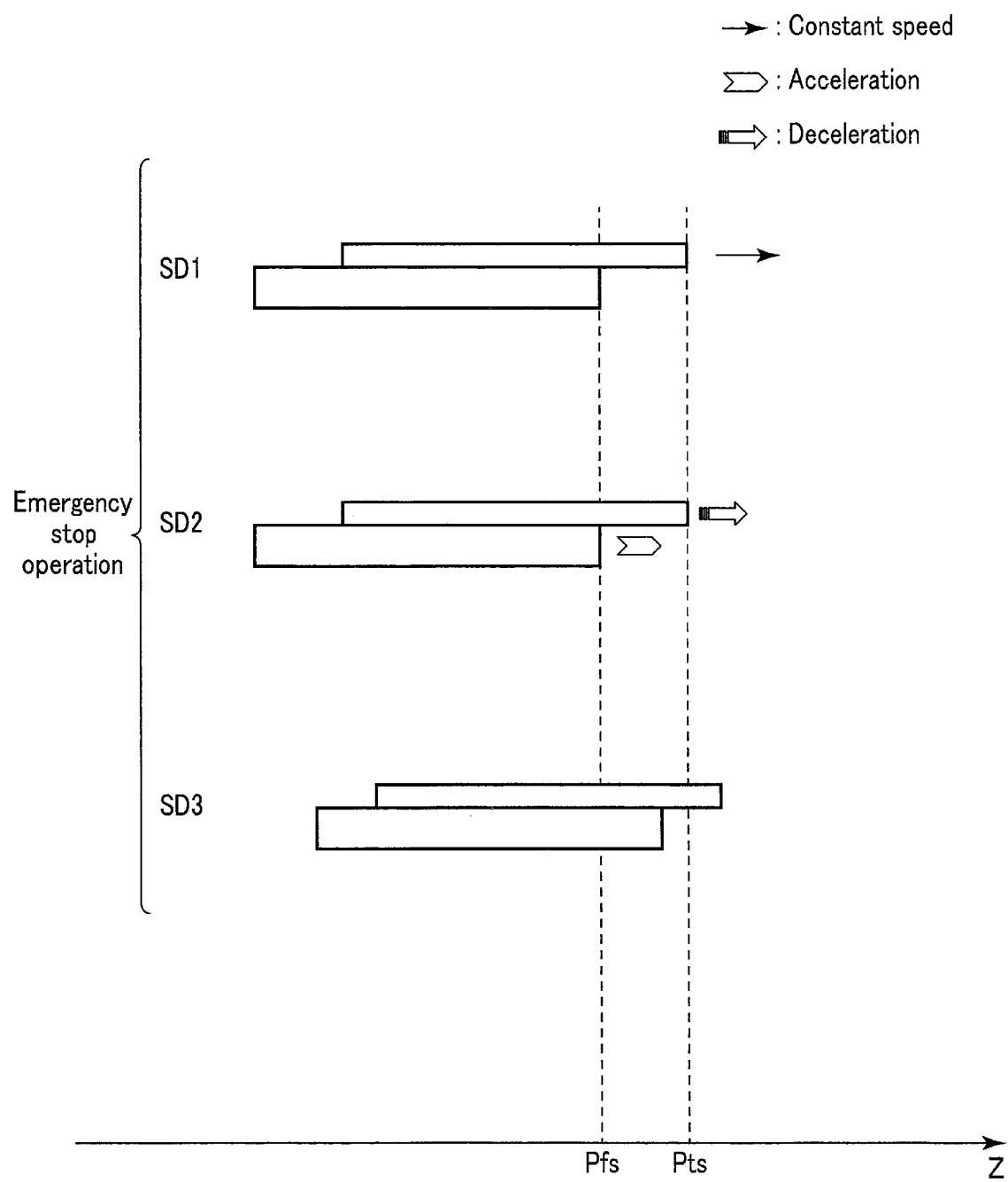
FIG. 14 is a view schematically showing the operations of the top and the upper frame in an emergency stop operation according to this embodiment.

FIG. 14 is a view schematically showing the operations of the top 51 and the upper frame 61 in an emergency stop operation according to this embodiment. Assume that, as shown in FIG. 14, when the top 51 is moved, an emergency stop instruction is input to the gantry control circuitry 33 (step SD1). An emergency stop instruction may be input from the input panel provided on the bed 23, may be input from the input device 105 of the console 100, or may be input from a service center connected to the console 100 via a network. When an emergency instruction is input, the gantry control circuitry 33 executes a stop auxiliary operation. That is, the gantry control circuitry 33 controls the top driving controller 62 and the frame driving controller 64 to accelerate the upper frame 61 in the forward direction while decelerating the top 51 relative to the upper frame 61 in the same direction (step SD2). Upon stopping the top 51 relative to the upper frame 61 while decelerating the upper frame 61, the gantry control circuitry 33 stops the upper frame 61 (step SD3).

This makes it possible to reduce impact on the object P caused by the emergency stop of the top.

The perceived speed reduction mode according to this embodiment can also be applied to an operation of immediately stopping the bed 23. The operations of the top 51 and the upper frame 61 at the time of an immediate stop will be described below. Note that an immediate stop indicates an operation of immediately stopping the operation of the bed 23 because of a human factor concerning, for example, the object P. A human factor indicates, for example, the contact of the object P or user with the top 51 at the time of sliding. In an immediate stop operation, the top 51 is preferably stopped at a position where the top 51 is located when an immediate stop instruction is input.

Figure 15:
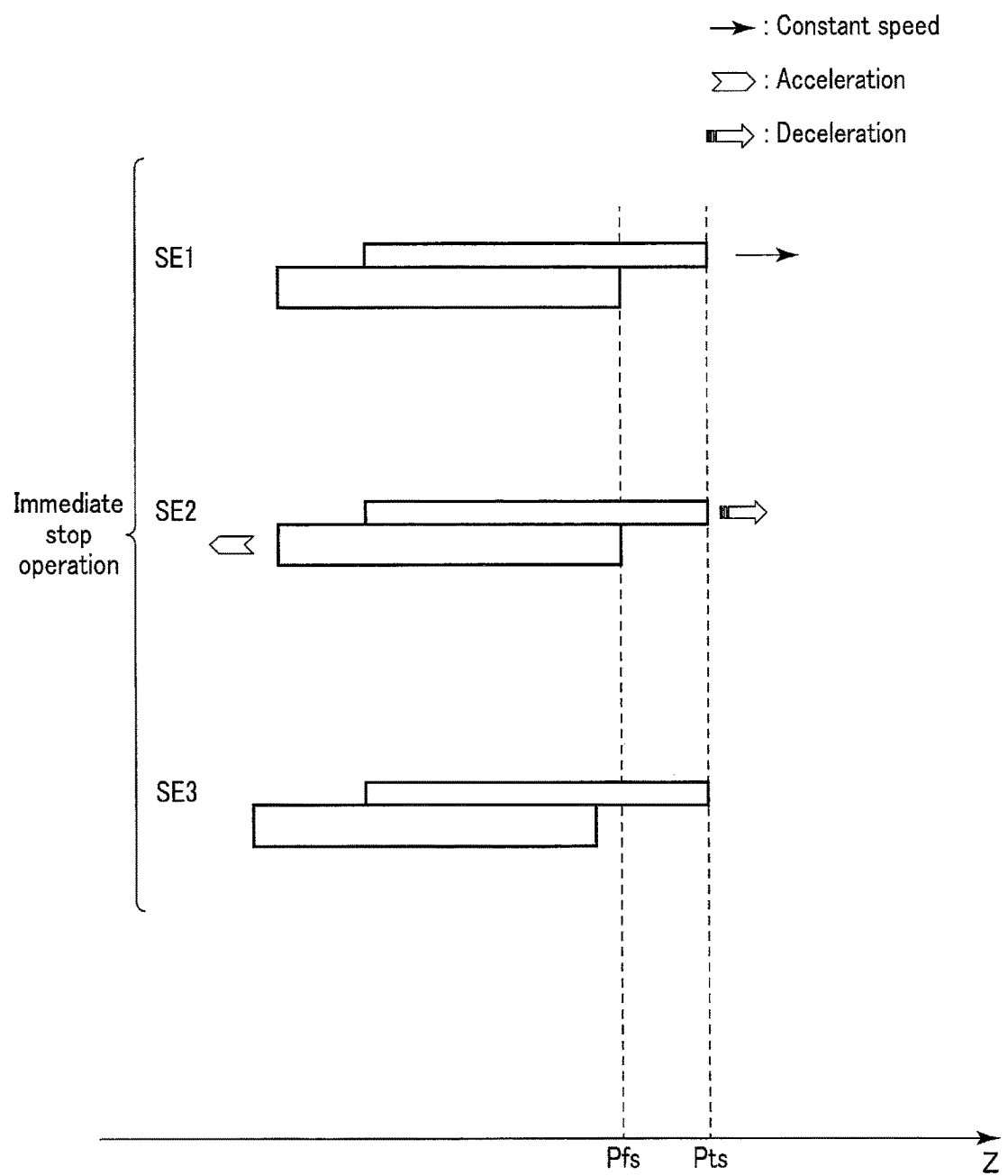
FIG. 15 is a view schematically showing the operations of the top and the upper frame in an immediate stop operation according to this embodiment.

FIG. 15 is a view schematically showing the operations of the top 51 and the upper frame 61 in an immediate stop operation according to this embodiment. Assume that, as shown in FIG. 15, when the top 51 is moved, an immediate stop instruction is input to the gantry control circuitry 33 (step SE1). An immediate stop instruction may be input from the input panel provided on the bed 23, may be input from the input device 105 of the console 100, or may be input from the service center connected to the console 100 via the network. In addition, when mechanical contact with a bed structure such as the top 51 or the upper frame 61 is detected, the gantry control circuitry 33 may generate an immediate stop instruction. When an immediate stop instruction is input or generated, the gantry control circuitry 33 executes an immediate stop auxiliary operation. That is, the gantry control circuitry 33 controls the top driving controller 62 and the frame driving controller 64 to accelerate the upper frame 61 in a direction opposite to the forward direction of the top 51 while decelerating the top 51 relative to the upper frame 61 along the forward direction (step SE2). Thereafter, the gantry control circuitry 33 controls the top driving controller 62 and the frame driving controller 64 to almost simultaneously stop the upper frame 61 and the top 51 (step SE3). In this case, the gantry control circuitry 33 adjusts the moving speeds of the top 51 and the upper frame 61 so as not to change the apparent position of the top in the time interval between the instant the immediate stop instruction is input and the instant the top 51 stops. This makes it possible to reduce the apparent slide distance of the top 51 while reducing the impact on the object P caused by the immediate stop of the top 51.

The above structure of the bed 23 is an example. This embodiment is not limited to this. For example, the bed 23 according to the embodiment may have any structure that allows top support structures such as the top 51 and the upper frame 61 to independently move in the Z direction. For example, a self-propelled support base that can independently move in the Z direction while slidably supporting the top 51 may be provided in place of the upper frame 61 and the support base 55.

The support base 55 of the bed 23 according to this embodiment includes the X link 65 that causes the upper frame 61 and the lower frame 63 to approach or separate from the gantry 10 accompanying lifting/lowering motion. However, this embodiment is not limited to this. The support base 55 according to the embodiment may include any lifting/lowering mechanism as long as it can lift or lower the upper frame 61 and the lower frame 63. For example, the embodiment may include an X link that lifts or lowers the upper frame 61 and the lower frame 63 while fixing the distances from them to the gantry 10 or another lifting/lowering mechanism other than an X link.

In the above description, both a start auxiliary operation and a stop auxiliary operation are performed in the perceived speed reduction mode. However, only one of a start auxiliary operation and a stop auxiliary operation may be performed.

According to the above arrangement, the X-ray computed tomography apparatus 1 according to this embodiment includes the gantry 10, the upper frame 61, the top driving controller 62, the frame driving controller 64, and the gantry control circuitry 33. The gantry 10 includes the X-ray tube 13 and the X-ray detector 15. The upper frame 61 supports the top 51, on which an object is placed, so as to allow the top 51 to move in the Z direction which is the longitudinal direction of the top 51. The top driving controller 62 moves the top 51 in the Z direction. The frame driving controller 64 moves the upper frame 61 in the Z direction. The gantry control circuitry 33 controls the top driving controller 62 and the frame driving controller 64 to execute at least one of a start auxiliary operation for accelerating the top 51 to a set speed and a stop auxiliary operation for stopping the top 51. In a start auxiliary operation, upon positioning the upper frame 61 at a moving start position decided based on scan conditions, the gantry control circuitry 33 controls the frame driving controller 64 to accelerate the upper frame 61 in the forward direction before moving the top 51 at the time of starting to move the object P in a scan. After the lapse of a predetermined time since the start of acceleration control on the upper frame 61 by the frame driving controller 64, the gantry control circuitry 33 controls the top driving controller 62 to accelerate the top 51 to a set speed along the forward direction. In a stop auxiliary operation, the gantry control circuitry 33 controls the frame driving controller 64 to accelerate the upper frame 61 along the forward direction at the time of decelerating the top 51. After the lapse of a predetermined time since the start of acceleration control on the upper frame 61 by the frame driving controller 64, the gantry control circuitry 33 controls the top driving controller 62 to stop the top 51.

According to a start auxiliary operation, it is possible to increase the slide distance of the top 51 relative to the upper frame 61 until the top 51 reaches a set high speed and to reduce the acceleration of the top 51 as compared with a case in which the upper frame 61 is fixed. Accordingly, this can reduce the load on the object P caused by acceleration. According to a stop auxiliary operation, it is possible to increase the slide distance of the top 51 relative to the upper frame 61 until the top 51 is stopped at an apparent position, and hence it is possible to reduce the deceleration of the top 51 (acceleration in the −Z direction) as compared with a case in which the upper frame 61 is fixed. Accordingly, this can reduce the load on the object P caused by deceleration. The length of the top 51 is preferably decided in consideration of the length of an acceleration/deceleration range as well as the length of a scan range. Providing the perceived speed reduction mode can reduce the length of an acceleration/deceleration range. Typically, this makes it possible to decrease the length of the top, and hence to downsize the bed 23.

According to at least one embodiment described above, it is possible to reduce the load on a patient caused by acceleration/deceleration of the top.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
a gantry including an X-ray tube and an X-ray detector;
a top support portion configured to support a top, on which an object is placed, so as to allow the top to move in a longitudinal direction of the top;
a first driving controller configured to move the top in the longitudinal direction;
a second driving controller configured to move the top support portion in the longitudinal direction; and
control circuitry configured to execute at least one of a start operation and a stop operation, the control circuitry being configured to control, for a start operation, the second driving controller to accelerate the top support portion along a forward direction before moving the top when starting to move the object in a scan after positioning the top support portion at a moving start position decided based on a condition for the scan and control the first driving controller to accelerate the top to a set speed along the forward direction after lapse of a first predetermined time since start of acceleration control on the top support portion by the second driving controller, and the control circuitry being configured to control, for a stop operation, the second driving controller to accelerate the top support portion along the forward direction when decelerating the top and control the first driving controller to stop the top after lapse of a second predetermined time since start of acceleration control on the top support portion by the second driving controller.

2. The X-ray computed tomography apparatus of claim 1, further comprising processing circuitry configured to determine, based on a scan range and the set speed, whether to execute at least one of the start operation and the stop operation.

3. The X-ray computed tomography apparatus of claim 2, further comprising an input device configured to designate the scan range with respect to a scanogram in accordance with an instruction from a user.

4. The X-ray computed tomography apparatus of claim 1, further comprising processing circuitry configured to determine, based on a comparison between an acceleration of the top which is estimated from a distance from an initial position to a scan start position and the set speed and an acceleration that is configured to be allowed by an object, whether to execute at least one of the start operation and the stop operation.

5. The X-ray computed tomography apparatus of claim 1, wherein when a stop instruction is issued while the top is moved, the control circuitry decelerates the top to stop the top and moves the top support portion in the same direction as a forward direction of the top.

6. The X-ray computed tomography apparatus of claim 1, wherein when a stop instruction is issued while the top is moved, the control circuitry decelerates the top to stop the top and moves the top support portion in a direction opposite to a forward direction of the top.

7. The X-ray computed tomography apparatus of claim 1, wherein the control circuitry calculates a distance that the top support portion is retracted from an initial position to the moving start position in the start operation based on a distance from the initial position to a scan start position and an acceleration that is configured to be allowed by an object.

8. The X-ray computed tomography apparatus of claim 1, wherein when accelerating the top support portion before moving the top in the start operation, the control circuitry moves the top support portion along the same direction as a forward direction of the top at a time of performing a scan.

9. The X-ray computed tomography apparatus of claim 1, wherein when accelerating the top support portion at a time of decelerating the top in the stop operation, the control circuitry moves the top support portion along the same direction as a forward direction of the top at a time of performing a scan.

10. The X-ray computed tomography apparatus of claim 1, wherein when reciprocating the top in a scan range, the control circuitry performs the start operation when accelerating the top to the set speed in each of a forward scan and a backward scan, and performs the stop operation when stopping the top.

11. The X-ray computed tomography apparatus of claim 1, further comprising processing circuitry configured to decide the moving start position based on a start position of a scan range and the set speed.

12. The X-ray computed tomography apparatus of claim 1, wherein in the start operation, the control circuitry controls the second driving controller to accelerate the top support portion along the forward direction while stopping the top relative to the top support portion after retracting the top and the top support portion to the moving start position, and when the top support portion reaches a predetermined speed, controls the first driving controller and the second driving controller to decelerate the top support portion and accelerate the top relative to the top support portion along a forward direction at a time of decelerating the top support portion.

13. The X-ray computed tomography apparatus of claim 1, wherein in the stop operation, the control circuitry controls the first driving controller and the second driving controller to accelerate the top support portion along the forward direction when decelerating the top while decelerating the top relative to the top support portion along the forward direction, controls, when the top support portion reaches a predetermined speed, the first driving controller and the second driving controller to decelerate the top support portion while decelerating the top relative to the top support portion, and controls the first driving controller and the second driving controller to stop the top relative to the top support portion when decelerating the top support portion.

14. A bed device comprising:
a top support portion configured to support a top, on which an object is placed, so as to allow the top to move in a longitudinal direction of the top;
a first driving controller configured to move the top in the longitudinal direction;
a second driving controller configured to move the top support portion in the longitudinal direction; and
control circuitry configured to execute at least one of a start operation of controlling the second driving controller to accelerate the top support portion along a forward direction before moving the top when starting to move the object in a scan after positioning the top support portion at a moving start position decided based on a condition for the scan and controlling the first driving controller to accelerate the top to a set speed along the forward direction after lapse of a first predetermined time since start of acceleration control on the top support portion by the second driving controller, and a stop operation of controlling the second driving controller to accelerate the top support portion along the forward direction when decelerating the top and controlling the first driving controller to stop the top after lapse of a second predetermined time since start of acceleration control on the top support portion by the second driving controller.

* * * * *